(12) United States Patent
Woodmansee, Jr. et al.

(10) Patent No.: US 9,980,909 B2
(45) Date of Patent: *May 29, 2018

(54) OXYGEN-ENABLED COMPOSITION

(71) Applicant: BAYLOR UNIVERSITY, Waco, TX (US)

(72) Inventors: John W. Woodmansee, Jr., Frisco, TX (US); Robert A. Woodmansee, Plano, TX (US); James R. Smith, Plano, TX (US)

(73) Assignee: Baylor University, Waco, TX (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/493,688

(22) Filed: Apr. 21, 2017

(65) Prior Publication Data

US 2017/0281544 A1    Oct. 5, 2017

Related U.S. Application Data

(63) Continuation-in-part of application No. 15/188,586, filed on Jun. 21, 2016.

(60) Provisional application No. 62/433,008, filed on Dec. 12, 2016, provisional application No. 62/315,524, filed on Mar. 30, 2016.

(51) Int. Cl.
    *A61K 9/14* (2006.01)
    *A61K 33/00* (2006.01)
    *A61K 9/00* (2006.01)
    *A61K 33/08* (2006.01)
    *C01F 7/02* (2006.01)
    *A61K 47/69* (2017.01)
    *A61K 9/16* (2006.01)

(52) U.S. Cl.
    CPC ............ *A61K 9/143* (2013.01); *A61K 9/0026* (2013.01); *A61K 33/00* (2013.01); *A61K 33/08* (2013.01); *A61K 47/6949* (2017.08); *C01F 7/02* (2013.01); *A61K 9/1611* (2013.01)

(58) Field of Classification Search
None
See application file for complete search history.

(56) References Cited

U.S. PATENT DOCUMENTS

| | | | | |
|---|---|---|---|---|
| 4,093,707 A * | 6/1978 | Merkl | ...................... | A61K 8/26 423/154 |
| 5,225,229 A * | 7/1993 | Martin | ..................... | C01F 7/144 423/625 |
| 9,649,335 B1 * | 5/2017 | Bruce | ..................... | A61K 33/08 |

OTHER PUBLICATIONS

Culver Class of 1952 Newsletter. https://alumni.culver.org/document.doc?id=517&chid=63, accessed May 17, 2017, printed Oct. 2013, 20 printed pages.*

BK Song, WH Nugent, CM Sayes, ED Bruce. "Effects of Novel Oxygen Therapeutic on Systemic and Microcirculatory Variables in Sprague-Dawley Rat Isovolemic Hemodilution Model." The FASEB Journal, vol. 30 No. 1, Supplement 946.11, Apr. 2016, 1 printed page.*

(Continued)

*Primary Examiner* — Isaac Shomer
(74) *Attorney, Agent, or Firm* — Culhane Meadows PLLC; Robert Klinger

(57) ABSTRACT

A composition of chlorine-free poly-oxygenated aluminum hydroxide that comprises a clathrate containing oxygen gas molecules. In one embodiment, the poly-oxygenated aluminum hydroxide has particles having a diameter of 212 microns or less. The composition may be homogeneous.

16 Claims, 8 Drawing Sheets

(56) References Cited

OTHER PUBLICATIONS

P Yang. "Investigating the efficacy of a novel therapeutic to mitigate traumatic brain injury : contributions of environmental exposures to overall healing." Abstract of Masters Thesis, Baylor University. https://baylor-ir.tdl.org/baylor-ir/handle/2104/9466?show=full, accessed Jun. 14, 2017, published Aug. 2015.*
J Gueldner, F Zhang, B Zechmann, ED Bruce. "Evaluating a Novel Oxygenating Therapeutic for Its Potential Use in The Advancement of Wound Healing." Toxicology in Vitro, 2017, doi: 10.1016/j.tiv.2017.06.005, pp. 1-32 and one initial page (33 sheets).*
AK Karamalidis, DA Dzombak. "Surface Complexation Modeling Gibbsite." ISBN 978-0-470-58768-3, pages included: title page, copyright page, and pp. 15-19 (Year: 2010).*
ChEBI:30188—hydroxidooxidoaluminum. https://www.ebi.ac.uk/chebi/searchId.do?chebild=30188, accessed by examiner on Sep. 28, 2017, 2 printed pages, last modified Jan. 4, 2006. (Year: 2006).*
Sun-Nation. Dr. George Merkl PhD. http://www.sun-nation.org/merkl-dr-george-merkl.html accessed by examiner Oct. 30, 2017. 11 printed pages. (Year: 2017).*
SJ Hultquist. "The Introduction of Negative Claim Limitations During Ex Parte Prosecution: 35 U.S.C. 112 and the Issue of Antecedent Support." http://www.hultquistip.com/files/negative_claims.pdf, accessed Dec. 4, 2017, 11 printed pages. (Year: 2017).*

* cited by examiner

Figure 5. Scanning Electron micrograph of Ox66™ particle following nano-engineering. Magnification = 8000x Figure 6. Scanning Electron micrograph of Ox66™ following nano-engineering. Magnification = 10,000x Figure 7. Scanning Electron micrograph of Ox66™ following nano-engineering. Magnification = 10,000x

Particle Size: 26-45 μm

|        | C     | O     | Al    | Cl   | (By % weight) |
|--------|-------|-------|-------|------|---------------|
| Spot 1 | 0.00  | 0.00  | 0.00  | 0.00 |               |
| Spot 2 | 56.80 | 35.02 | 8.18  | 0.00 |               |
| Spot 3 | 0.00  | 0.00  | 38.40 | 0.00 | **F           |
| Spot 4 | 63.12 | 30.14 | 6.74  | 0.00 |               |
| Spot 5 | 0.00  | 33.91 | 6.93  | 0.00 |               |

Particle Size: 46-106 μm

|        | C    | O     | Al    | Cl   | (By % weight) |
|--------|------|-------|-------|------|---------------|
| Spot 1 | 0.00 | 54.49 | 39.35 | 0.00 | **F           |
| Spot 2 | 1.90 | 55.46 | 37.55 | 0.00 | **F           |
| Spot 3 | 1.34 | 60.58 | 36.74 | 0.00 | **F           |
| Spot 4 | 0.00 | 57.12 | 42.88 | 0.00 |               |

Particle Size: 107-212 μm

|        | C    | O     | Al    | Cl   | (By % weight) |
|--------|------|-------|-------|------|---------------|
| Spot 1 | 0.00 | 58.22 | 34.64 | 0.00 | *F            |
| Spot 2 | 0.00 | 56.08 | 36.26 | 0.00 | *F            |
| Spot 3 | 0.00 | 62.85 | 37.15 | 0.00 | *F            |

Particle Size: 300-425 μm

|        | C    | O     | Al    | Cl    | (By % weight) |
|--------|------|-------|-------|-------|---------------|
| Spot 1 | 0.00 | 41.72 | 41.75 | 16.53 |               |
| Spot 2 | 0.00 | 53.53 | 31.01 | 15.46 |               |
| Spot 3 | 0.00 | 57.41 | 25.74 | 16.85 |               |
| Spot 4 | 0.00 | 54.62 | 29.29 | 16.10 | *F            |

Particle Size: 426-500 μm

|        | C     | O     | Al    | Cl    | (By % weight) |
|--------|-------|-------|-------|-------|---------------|
| Spot 1 | 82.05 | 17.95 | 0.00  | 0.00  |               |
| Spot 2 | 0.00  | 59.26 | 26.07 | 14.67 |               |
| Spot 3 | 0.00  | 49.57 | 18.42 | 32.00 |               |
| Spot 4 | 0.00  | 29.16 | 25.31 | 45.52 | *F            |

FIGURE 8

OXYGEN-ENABLED COMPOSITION

CLAIM OF PRIORITY

This application claims priority under 35 U.S.C. Section 119 of U.S. Provisional Patent Application Ser. No. 62/433,008 entitled Oxygen-Enabled Composition filed Dec. 12, 2016, and is a Continuation-in-Part of U.S. patent application Ser. No. 15/188,586 filed Jun. 21, 2016, entitled Process for Generating Nanometer Sized Particles That Increase Oxygen Levels in Mammalian Tissues, which application claims priority under 35 U.S.C. Section 119 of U.S. Patent Application U.S. Ser. No. 62/315,524 entitled OXYGEN-ENABLED RESUSCITATIVE FLUID filed Mar. 30, 2016, the teachings of which are incorporated herein by reference in their entirety.

TECHNICAL FIELD

The disclosure relates generally to a poly-oxygenated aluminum hydroxide composition suitable for advanced therapies when delivered to mammals, including humans and animals. Principal delivery methods include topical, oral, anal, vaginal, inhalation, intramuscular injection, and intravenous delivery.

BACKGROUND

Oxygen is one of the fundamental building blocks of life. Oxygen sustains life, but it also has therapeutic (i.e. healing) powers when delivered topically to tissue, orally for digestion, anally, vaginally, aerosolized for inhalation, injected to intramuscular tissue, intravenously to the blood circulatory system, and other delivery methods. Conventional oxygen therapies are commonly comprised of a gaseous delivery of oxygen (i.e. $O_2$) in chambers, such as hyperbaric oxygen therapy (HBOT). However, the concentration of oxygen delivered by gas is rather small, and the chambers are both expensive and not widely available.

A poly-oxygenated aluminum hydroxide, such as manufactured by Hemotek, LLC of Plano, Tex. as Ox66™, the Assignee of this application, is a clathrate containing oxygen gas molecules that has been proven to have numerous therapeutic benefits. The Ox66™ composition is provided in powder form and is described as a non-homogenous size particle population, typically ranging from about 50 to 800 micrometers (μm).

Ox66™ exists under STP (standard temperature and pressure) as a clathrate. A clathrate is a chemical substance consisting of a lattice that traps or contains molecules. The molecules trapped or contained within the Ox66™ clathrate are oxygen gas ($O_{2(g)}$). The molecular formula of Ox66™ is $Al_{12}H_{42}O_{36}$, which mathematically reduced is $Al(OH)_3.6O_2$. The 6 free oxygen gas molecules ($O_{2(g)}$) are separate from the oxygen molecules covalently bound in the hydroxide complex.

SUMMARY

A composition of chlorine-free poly-oxygenated aluminum hydroxide that comprises a clathrate containing oxygen gas molecules. In one embodiment, the poly-oxygenated aluminum hydroxide has particles having a diameter of 212 microns or less. The composition may be homogeneous.

BRIEF DESCRIPTION OF THE FIGURES

FIG. 8 is a chart illustrating the filtered Ox66™ composition at different particle sizes, obtained using a Scanning Electron Microscope (SEM) with Energy-dispersive X-ray spectroscopy (EDS) analyzing various spots of the filtered Ox66™ composition.

DETAILED DESCRIPTION

Figure 1:
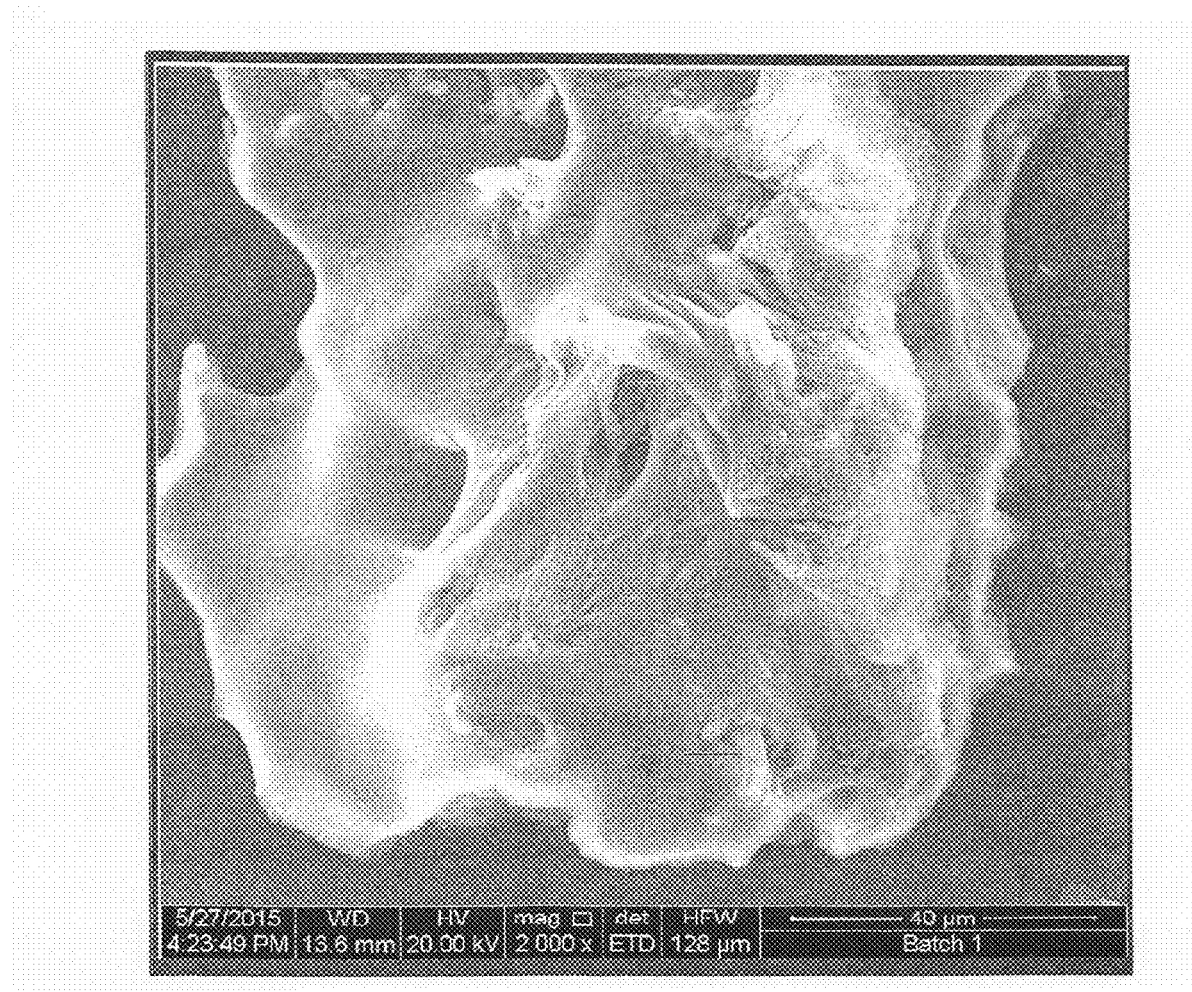
FIG. 1 is a scanning electron microscopy (SEM) image of a single 50 micrometer (μm) Ox66™ particle.

The following description of example embodiments provides information that enables a person skilled in the art to make and use the subject matter set forth in the appended claims, but may omit certain details already well-known in the art. The following detailed description is, therefore, to be taken as illustrative and not limiting. Objectives, advantages, and a preferred mode of making and using the claimed subject matter may be understood best by reference to the accompanying drawings in conjunction with the following detailed description of illustrative embodiments.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Nanoparticles are routinely defined as particles with sizes between about 1 and 1000 nm that show physical or chemical properties that are not found in bulk samples of the same material.

Dissolved oxygen refers to micrometer or nanometer sized bubbles of gaseous oxygen (mixed in water or other aqueous solution) made bioavailable to organisms, animals, or humans for respiration.

Aqueous medium means pertaining to, related to, and similar to water (the most common solvent on Earth).

Particles having a diameter of less than or equal to 70 nm do not create an immune response of the mammal.

Ox66™ particles are non-toxic poly-oxygenated aluminum hydroxide complexes comprising a clathrate containing oxygen gas molecules, stored in either a 1-99% by weight aqueous solution or as a dried powder, and are available from Hemotek LLC of Plano, Tex. The material is non-flammable, water-soluble, and slightly basic. Particle diameter sizes typically vary between 50 and 800 μm. These particles can also be described as a non-corrosive and non-vapor producing powder. Its appearance is white to slightly blue as a powder with mass but very little weight (i.e. one gallon weighs less than 4.3 ounces) or a clear slightly viscous liquid when placed in an aqueous suspension.

The inventive concepts disclosed and claimed in this application relate generally to a chlorine-free poly-oxygenated aluminum hydroxide composition comprising a clathrate containing oxygen gas molecules, comprising particles having a diameter of less than or equal to 212 µm. These chlorine-free particles having a diameter of less, than or equal to 212 µm enable numerous revolutionary applications and treatments that provide significant achievements in bioscience. Through research and clinical studies, these particles have been proven to treat body conditions of mammals, including humans and animals, with astounding success and efficiency. This will be described in more detail with, respect to FIG. 8 shortly.

According to exemplary embodiments of this disclosure, through research, studies and clinical studies, it has been discovered that engineering the Ox66™ particles to have diameter sizes at or below 3 µm opens up significant and revolutionary new opportunities for oxygen therapy. Providing particles having diameters of 3 µm is critical to achieve numerous new applications, such as by oral, nasal, intravenous and topical delivery, to treat conditions and diseases in revolutionary ways. Several of the new applications and treatments are disclosed herein.

One exemplary embodiment is delivering poly-oxygenated aluminum hydroxide particles intravenously as a resuscitative fluid, and to treat diseases of organs when the diameter of the particles is in the range of 250 nm to 1000 nm. Particles having diameters between 250 to 1000 nm will stay in the capillary, vein, or artery linings of the circulatory system and not passively diffuse past the lining, into surrounding tissue.

Another exemplary embodiment is delivery, by aerosol when inhaled, for absorption of the poly-oxygenated aluminum hydroxide particles through the lung tissue when the particles are reduced to 250 nm and less. Such an application effectively treats internal burns. Particles having a diameter size from 1 to 3000 nm deposit into the deep airway ducts and diffuse evenly within the alveolar or gas exchange regions of the lung.

A remarkable example is delivering the poly-oxygenated aluminum hydroxide particles intravenously to treat traumatic brain injury (TBI) when the diameter of the particles is reduced to about 10 nm and less so that the particles can traverse the brood brain barrier (BBB). This application can also be used to treat strokes, chronic traumatic encephelopathy (CTE), and perhaps even cancer.

There is a significant biophysical difference between a 50 µm particle and a 3 µm particle. After intravenous administration, 50 µm particles are larger and have more mass than 3 µm particles, therefore they tend to absorb onto the linings of the veins. Three (3) µm particles stay in circulation much longer, have much less mass, and have higher surface area. After inhalation administration, 50 µm diameter particles deposit in the oral or nasal cavity and do not reach even the upper airways of the lung. Three (3) µm diameter particles are small enough to deposit in the very deep lung and perfuse out to the lung lining. After topical administration, 50 µm diameter particles tend to stay on the surface of the epidermis and eventually wash off the skin completely. Three (3) µm diameter particles penetrate through the epidermis and dermis layers of the skin and reside in the subcutaneous layer of the skin. After oral administration, 3 µm diameter particles absorb through the lining of the esophagus and stomach. Fifty (50) µm diameter particles reside in the stomach for up to 4 hours, dissolve (or break-down) and lose their oxygen carrying capability.

Another exemplary embodiment includes increasing the oxygen content of fluids with nanometer-sized Ox66™ particles, such as water, sports drinks, and nutritional drinks, which provides many benefits and applications. The nanometer-sized Ox66™ particles have been clinically shown to pass through the stomach, duodenum, and intestinal walls into the bloodstream of the body, and are not simply absorbed by the stomach lining. One method for increasing the dissolved oxygen content in an aqueous medium includes sparging the aqueous medium with air, oxygen or oxygen-enriched air.

In another exemplary embodiment, the nanometer-sized Ox66™ particles, either as a powder or in a carrier such as a gel or lotion, have also been clinically proven to increase the level of localized oxygen in injured tissues to accelerate the healing process.

FIG. 1 is a scanning electron microscopy (SEM) image of a single 50 micrometer (µm) Ox66™ particle. A 50 µm particle is easily aerosolized, but it is well outside the respirable range of 1-3 µm. A 50 µm particle has little density due to its chemical composition and its porosity.

Figure 2:
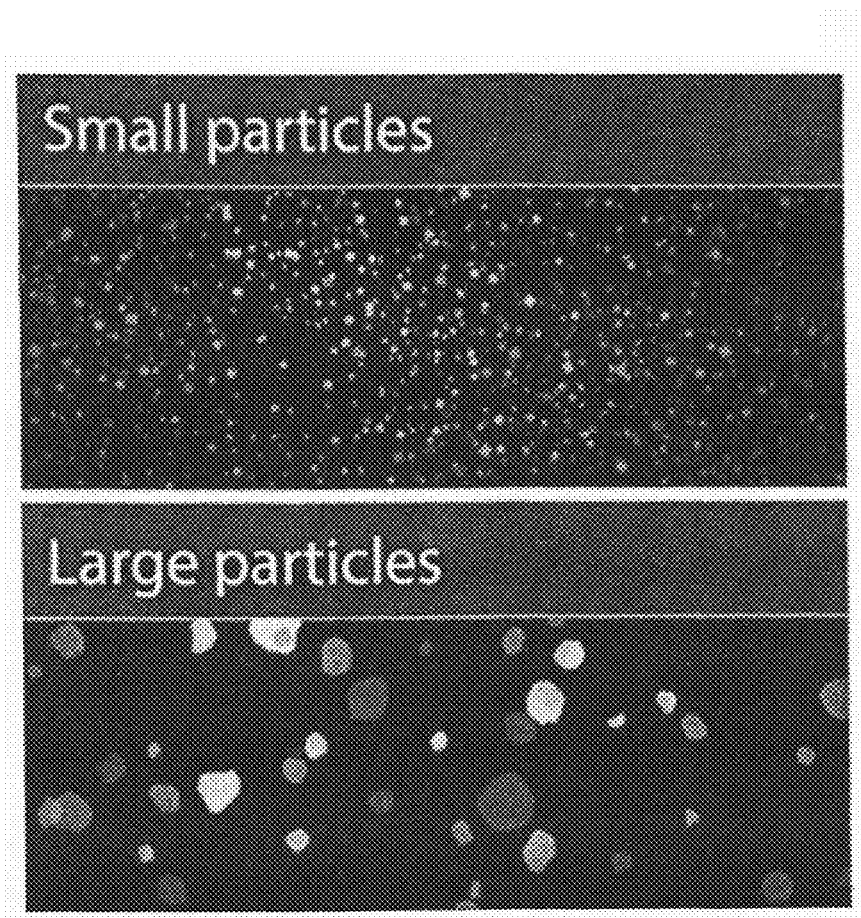
FIG. 2 is a graphic art image of the jagged shaped Ox66™ particle population.

FIG. 2 is a graphic art image of the jagged shaped Ox66™ particle population.

DESCRIPTION OF EXAMPLE EMBODIMENTS

Controlled milling is defined as a machining procedure using vessels accelerating in a rotary or planetary motion to decrease the size of the primary particles from micrometer sized to nanometer sized materials. Milling covers a wide array of procedures, operations, tools, and machines. The resultant nanometer sized particle can be accomplished using small instruments or large milling machines. Example milling instruments include: "milling machine", "machining centers", or "multitasking machines".

Figure 3:
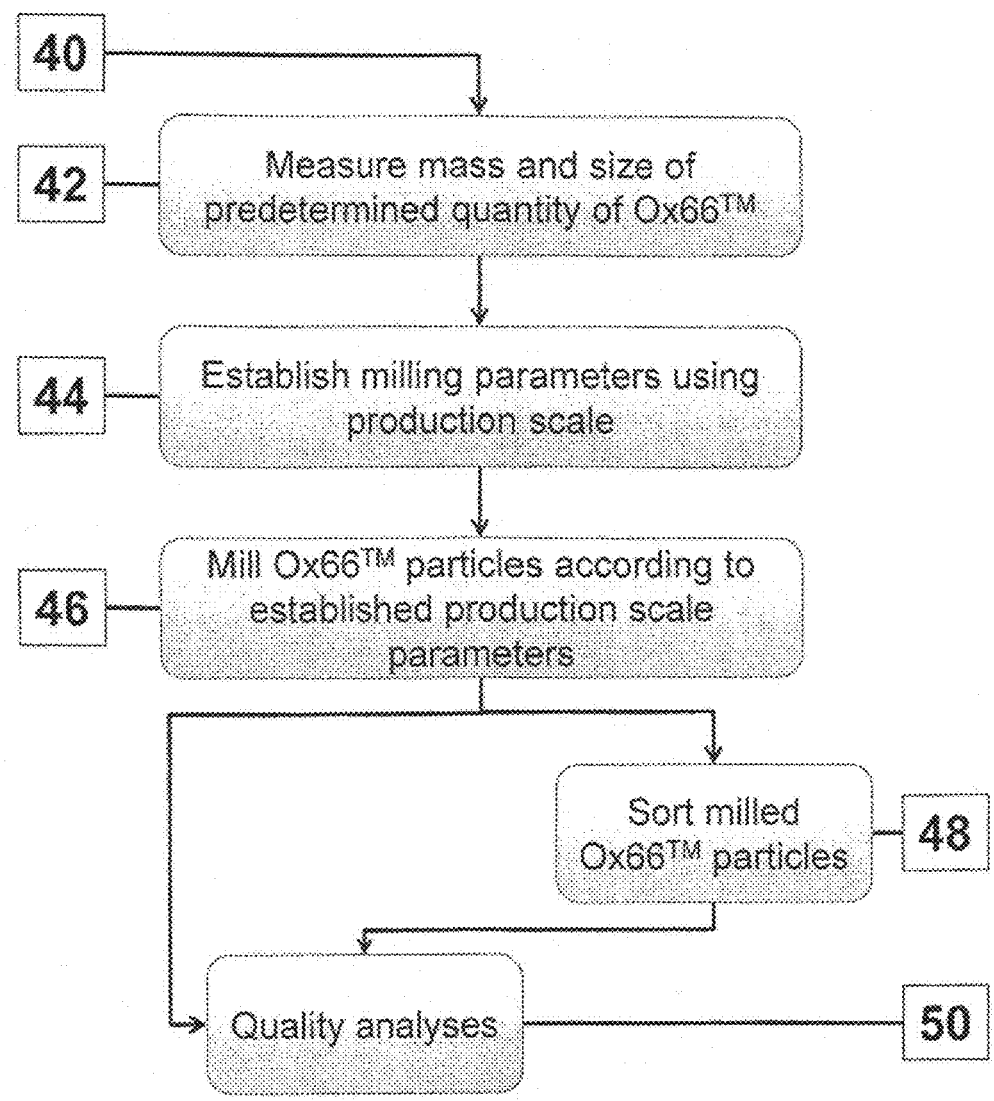
FIG. 3 depicts one exemplary process used to create nano-engineered Ox66™ nanoparticles to exploit the physical and chemical properties of each particle-type.

Referring to FIG. 3, there is shown an exemplary process at 40 for forming nanosized Ox66™ particles having diameter sizes of 3 µm or less using a planetary motion milling machine.

At step 42, a predetermined quantity of the quality assured Ox66™ powdered material is measured, and placed in a container.

Figure 5:
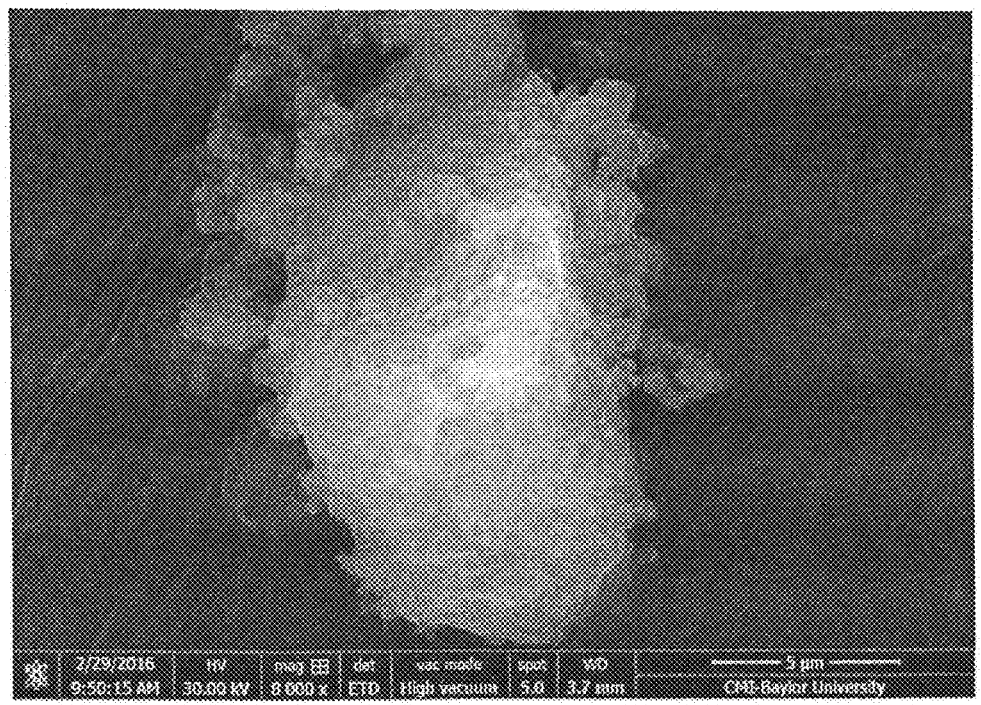
FIGS. 5-7 are scanning electron microscopy (SEM) images showing, the nano-engineered Ox66™ particles at different image magnifications having particle diameters at 3 μm and below.

At step 44, a milling scale is used to establish parameters of the generating particles having a diameter of 3 µm or less, such as shown in FIG. 5, both for small-scale production as well as mass production. The milling procedure is dependent upon the features of the ball mill, which may be a planetary motion device, such as Retsch Planetary Ball Mill PM 100, 200, or 400 or United Nuclear Scientific Equipment 'Hobby" Ball Mill. The milling procedure identifies several variables, including a quantity of Ox66™ material, the rotation rate, the size of the milling beads, the type of milling beads, and the time of milling to achieve desired size of the Ox66™ particles. For example, the rotation rate may be for at least 1 minute up to 1,440 minutes at a rotation rate of at least 100 up to 10,000 rotations per minute.

Figure 4:
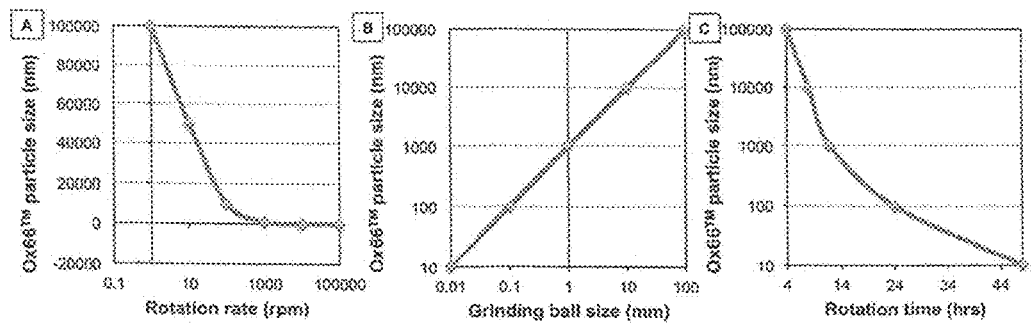
FIG. 4 illustrates three different graphs modeling the effect of Ox66™ particle size when varying (A) rotation rate, (B) grinding ball size, and (C) rotation time.

FIG. 4 includes three different graphs modeling the effect of Ox66™ particle size when varying (A) rotation rate, (B) grinding ball size, and (C) rotation time. As rotation rate, measured in rotations per minute (rpm) increases, particle size decreases. As grinding ball size, measured in millimeters (mm) decreases, particle size decreases. As rotation time, measured in hours (hrs) increases, particle size decreases.

At step 46, the predetermined quantity of Ox66™ particles are then milled in a controlled manner in a planetary motion ball mill, according to the milling procedure to achieve a desired homogenous size of the Ox66™ particles. The Ox66™ particles are milled or ground down under high energy in the presence of a milling media, such as highly reticulated polystyrene or zirconium milling beads. The Ox66™ particles are recirculated, re-milling them until a consistent product is generated.

Optionally, at step 48, additional sorting may be performed.

At step 50, the homogeneous milled Ox66™ particles are subjected to quality analysis to confirm sizing and consistency. If the Ox66™ particles are not consistent, they may be further milled to achieve the desired sizing.

The milling media can also abrade under the conditions of milling, so care is taken such that significant contamination of the nanosuspension by the milling media does not occur. Nanosuspension is defined as a submicron colloidal dispersion of drug particles.

The resultant Ox66™ particles have a primary particle size of 3 µm or less. In one exemplary embodiment, the reduced size particles are then separated into homogeneous sizes in an effort to exploit the physical and chemical properties of each particle-type. Sieves can be used to sort out particles by sizes to create homogenous sizes of particles, such as sieve shakers manufactured by Endecotts Ltd of London, UK. Different size sieve filters are used to obtain selected particle sizes.

One homogenous size of particles may be particularly beneficial for treating a particular body condition, such as 10 µm diameter particles to treat traumatic brain injury (TBI). Another homogenous size of particles may be beneficial for providing a resuscitative fluid (RF) to increase the tissue oxygenation ($PO_2$), such as using 35 to 70 nm diameter particles which do not trigger an immune response. Generating nanometer sized particles increases the in vivo (i.e. in a whole, alive organism) dissolution rate and fraction absorbed to increases oral bioavailability.

Figure 6:
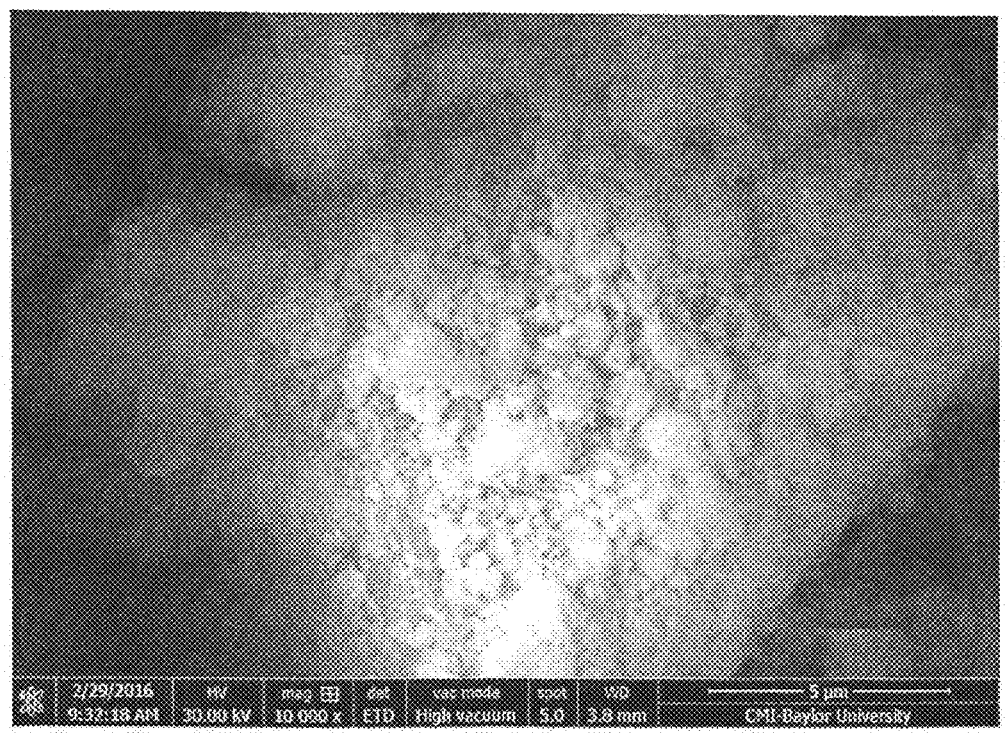
Figure 7:
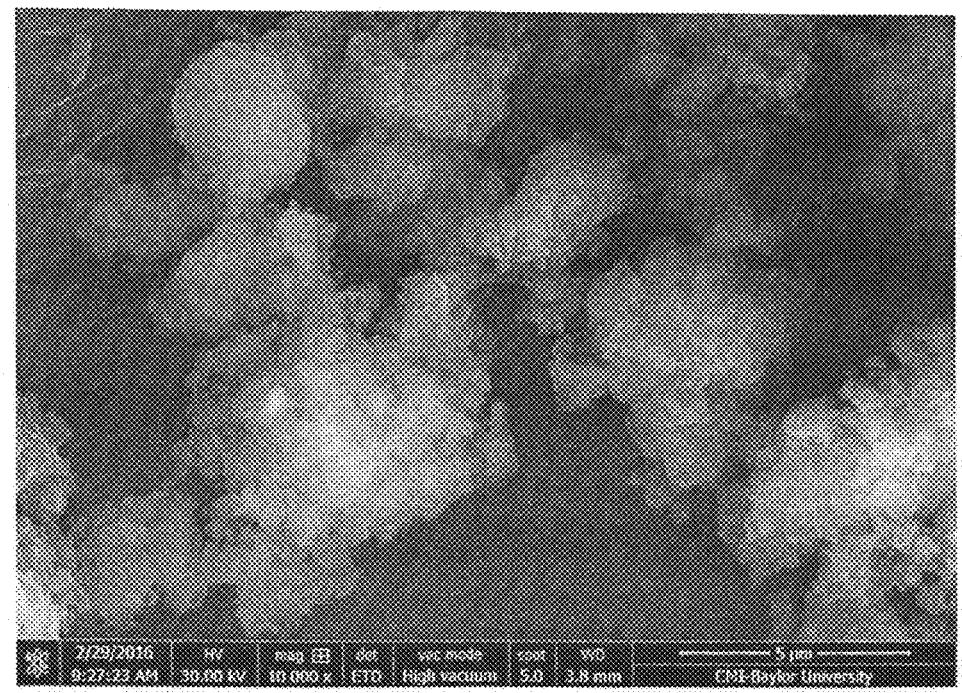

FIGS. 5-7 are scanning electron microscopy (SEM) images showing the nano-engineered Ox66™ particles at different image magnifications, showing the particle diameters at 3 µm and below.

The pharmaceutical preparation of nanomaterial-based dosage forms is encouraged by a number of pharmaceutical drivers; for compounds whose water solubility or dissolution rate limits their oral bioavailability, size reduction into the nanometer size domain can increase in vivo dissolution rate and fraction absorbed.

The process to generate a homogeneous nanometer size particle population can also be of use in the design of parenteral dosage forms wherein poorly soluble drugs can be "milled" to a specified size and size range resulting in not only useful bioavailability but also sustained release features.

The development of drug particles within the nanometer size regime of 1 to 1000 nm involves a top-down approach in which the active ingredient is milled (or otherwise subjected to particle reduction strategies) in either an aqueous environment or in a dry formulation; top-down strategies are considered more controllable and more robust as a function of process and design space for this type of manipulation.

Chlorine-Free Poly-Oxygenated Aluminum Hydroxide

Referring now to FIG. 8, according to another embodiment of this disclosure, a composition of chlorine-free poly-oxygenated aluminum hydroxide comprising a clathrate containing oxygen gas molecules is provided. The chlorine-free, composition is beneficial in a therapeutic quantity when delivered to a mammal, including, but not limited to, oral, topical, nasal, vaginal, anal, and intravenously administration. The composition is poly-oxygenated because it has oxygen gas ($O_{2(g)}$) that is free to move in the composition molecules, and which oxygen gas is bioavailable to oxygenate the mammal.

In one exemplary embodiment, the chlorine-free poly-oxygenated aluminum hydroxide is a composition of filtered Ox66™ composition. The poly-oxygenated aluminum hydroxide composition is free of chlorine residuals and may be homogeneous. Homogeneous as used in this application means that the sizes of the particles fall in a tight range of sizes, such as between 107-212 µm, 46-106 µm, and 26-45 µm. It has been discovered that Ox66™ particles having a diameter of less than or equal to about 212 µm are free of chlorine residuals and particles. Applicant sorted the Ox66™ composition by size into batches, and discovered that filtered particles having a diameter less than about 212 µm had a noticeably different texture and feel. Upon further investigating using a calibrated Scanning Electron Microscope (SEM) laboratory instrument to analyze various spots of the composition for different size ranges, it was discovered that such particles under 212 µm were free of chlorine particles and residuals, as supported in the test results shown in FIG. 8.

The composition comprising chlorine-free particles having diameters sized at or below 212 µm have tremendous uses in products, treatments and, therapies. For instance, the chlorine free composition is not a desiccant, which makes it ideal in some products, including cosmetics where maintaining moisture is preferred. A desiccant is a hygroscopic substance that induces or sustains a state of dryness (desiccation) in its vicinity. Commonly encountered pre-packaged desiccants are solids that absorb water. Chlorine is fairly reactive with water and oxygen and acts as a desiccant in particle systems. The Ox66™ composition is often, but not always, better suited when chlorine is absent in the formulation because of the desire to maximize the amount of oxygen in the product to improve efficacy. Cosmetic products including creams, moisturizers, serums, etc. tremendously benefit from the oxygen carrying properties of the Ox66™ composition, as well as the chlorine free composition of this disclosure.

It is noted that for larger particle suspensions in water, chlorine may be desired for stability. A formulation without chlorine is a more simple and streamlined compound that saves time, money, and resources.

A quantity of such chlorine-free particles has a softer feel and is less abrasive than the composition including chlorine, making the composition suitable for cosmetics that have demanding requirements from both manufacturers and customers.

In one exemplary embodiment, the chlorine-free composition is particularly well suited for use with or in nutraceuticals, including products configured to be orally ingested by a mammal. A nutraceutical is defined as a pharmaceutical-grade and standardized nutrient. Such nutraceuticals include, but are not limited to, baby formula, electrolytes, and supplements, such as Similac®, PediaSure®, Pedialyte®, Glucerna®, and Ensure® manufactured by Abbott Labs of Abbot Park, Ill., each of which are U.S. Registered trademarks of Abbott Labs. Other nutraceuticals can include, but are not limited to, performance enhancing products including Gatorade® branded products including fluids, powders, and bars.

In one exemplary embodiment, the chlorine-free composition is also particularly well suited as a poly-oxygenated metal hydroxide that is intravenously (IV) deliverable to a mammal. Such IV deliverable products can include 75-90% colloid or crystalline solution with 10-25% addition of poly-oxygenated metal hydroxide particles. The poly-oxygenated metal hydroxide may have a concentration range of 0.1 mg/l to 1000 mg/l. The poly-oxygenated metal hydroxide may have particles that are surface modified.

In one example method of use, the chlorine-free composition is therapeutically beneficial to treat a depletion of hemoglobin in the mammal, wherein the poly-oxygenated metal hydroxide acts as an oxygen resuscitative fluid to treat hypoxia, increasing the interstitial tissue oxygenation $P_{ISF}O_2$.

In other exemplary embodiments, products may include the chlorine-free composition in wound care, hair care, and skin care products. Such wound care products are configured to promote and accelerate the healing of skin wounds and lesions. Hair care products are configured to reduce baldness and re-grow hair, as the bioavailable oxygen gas is beneficial to stimulate growth, of hair follicles which may be oxygen deprived. Skin care products can include lotions, gels and soaps, for example, that treat skin conditions, such as psoriasis and eczema.

Again referring to the chart of FIG. 8 illustrating the composition of filtered Ox66™ at different particle sizes, there is shown five tables, obtained using a Scanning Electron Microscope (SEM) with Energy-dispersive X-ray spectroscopy (EDS).

As shown in the bottom table in FIG. 8, the data obtained from analyzing four (4) spots of the Ox66™ composition in a batch of homogeneous Ox66™ particles each having a diameter between 426-500 μm is shown. The first spot reflects analyzing the substrate having carbon. The data from analyzing the other 3 spots shows the percentage of chlorine varying between 14.67% and 45.52%, which is very significant.

As shown in the table second from the bottom of FIG. 8, the data obtained from analyzing four (4) spots of the Ox66™ composition in a batch of homogeneous Ox66™ particles having a diameter between 300-425 um is shown. The data From analyzing the 4 spots shows the percentage of chlorine varying between 15.46% and 16.85%. These are significant percentages of chlorine, and the chlorine is undesirable in many products, treatments and therapies as they can create adverse results and reactions.

As shown in the three upper tables in FIG. 8, the data obtained from analyzing spots of the Ox66™ composition in different batches of Ox66™ particles having, a diameter of Less than 212 μm shows the composition is entirely free of chlorine in all spots. This is true for the batches of homogeneous Ox66™ particles having a diameter between 26-45 μm, 46-106 μm, and 107-212 μm, as shown. This is significant and highly beneficial as previously described.

It is noted the detected carbon component in some samples is part of the substrate media that the composition is prepared upon during testing, and the carbon is not part of the Composition itself.

As provided in, more detail in the U.S. Provisional patent application U.S. Ser. No. 62/315,524 entitled OXYGEN-ENABLED RESUSCITATIVE FLUID filed Mar. 30, 2016, the teachings of which are incorporated herein by reference in their entirety as shown in paragraph [0001], the Ox66™ composition is:

configured to be therapeutically effective in treating a condition of a mammal;

configured to be intravenously delivered to a mammal, such as to oxygenate the mammal:

configured to not create an immune response of the mammal;

configured to penetrate through epidermis and dermis layers of skin and reside in a subcutaneous layer of the skin;

configured to absorb through lining of an esophagus and a stomach;

configured to traverse a brood brain barrier (BBB) of a mammal; and configured to stay in a capillary, vein, or artery linings of a mammal circulatory system and not passively diffuse past, a lining into surrounding tissue.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A composition, comprising:
a quantity of poly-oxygenated aluminum hydroxide comprising a clathrate containing oxygen gas molecules that is chlorine-free, wherein the poly-oxygenated aluminum hydroxide comprises particles each having a diameter of less than or equal to 212 μm.

2. The composition as specified in claim 1, wherein the poly-oxygenated aluminum hydroxide is homogeneous.

3. The composition as specified in claim 2, wherein the particles each have a diameter in the range of 107-212 um.

4. The composition as specified in claim 2, wherein the particles each have a diameter in the range of 46-106 um.

5. The composition as specified in claim 2, wherein the particles each have a diameter in the range of 26-45 um.

6. A quantity of poly-oxygenated aluminum hydroxide comprising a clathrate containing oxygen gas molecules that is chlorine-free, wherein the composition is not a desiccant.

7. A quantity of poly-oxygenated aluminum hydroxide comprising a clathrate containing oxygen gas molecules that is chlorine-free, wherein the poly-oxygenated aluminum hydroxide is configured to be intravenously delivered to a mammal.

8. A quantity of poly-oxygenated aluminum hydroxide comprising a clathrate containing oxygen gas molecules that is chlorine-free, wherein the poly-oxygenated aluminum hydroxide is configured to not create an immune response of a mammal.

9. The composition as specified in claim 8 wherein poly-oxygenated aluminum hydroxide is configured to be therapeutically effective in treating a condition of the mammal.

10. A quantity of poly-oxygenated aluminum hydroxide comprising a clathrate containing oxygen gas molecules that is chlorine-free, wherein the poly-oxygenated aluminum hydroxide is configured to deposit deep into a lung and perfuse out the lining of the lung.

11. A quantity of poly-oxygenated aluminum hydroxide comprising a clathrate containing oxygen gas molecules that is chlorine-free, wherein the poly-oxygenated aluminum hydroxide is configured to penetrate through epidermis and dermis layers of skin and reside in a subcutaneous layer of the skin.

12. A quantity of poly-oxygenated aluminum hydroxide comprising a clathrate containing oxygen gas molecules that is chlorine-free, wherein the poly-oxygenated aluminum hydroxide is configured to absorb through lining of an esophagus and a stomach.

13. A quantity of poly-oxygenated aluminum hydroxide comprising a clathrate containing oxygen gas molecules that is chlorine-free, wherein the poly-oxygenated aluminum hydroxide is configured to traverse a brood brain barrier (BBB) of a mammal.

14. A quantity of poly-oxygenated aluminum hydroxide comprising a clathrate containing oxygen gas molecules that is chlorine-free, wherein the poly-oxygenated aluminum hydroxide is configured to stay in a capillary, vein, or artery linings of a mammal circulatory system and not passively diffuse past a lining into surrounding tissue.

15. A composition, comprising:
 a quantity of poly-oxygenated aluminum hydroxide comprising a clathrate containing oxygen gas molecules that is chlorine-free,
 wherein the composition comprises particles each having a diameter of less than or equal to 212 μm; and
 wherein the quantity of poly-oxygenated aluminum hydroxide is homogeneous.

16. The composition of claim 15, wherein the composition is made by a process that filters a quantity of a poly-oxygenated aluminum hydroxide.

* * * * *